United States Patent
Ohtsu et al.

(10) Patent No.: US 9,611,461 B2
(45) Date of Patent: Apr. 4, 2017

(54) ENTEROBACTERIACEAE BACTERIA EXHIBITING INCREASED L-CYSTEINE PRODUCING ABILITY

(71) Applicant: National University Corporation Nara Institute of Science and Technology, Ikoma-shi, Nara (JP)

(72) Inventors: Iwao Ohtsu, Ikoma (JP); Takeshi Nakatani, Ikoma (JP); Ai Tamakoshi, Ikoma (JP); Sayo Takahashi, Ikoma (JP); Hiroshi Takagi, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 7 days.

(21) Appl. No.: 14/777,880

(22) PCT Filed: Mar. 14, 2014

(86) PCT No.: PCT/JP2014/056872
§ 371 (c)(1),
(2) Date: Sep. 17, 2015

(87) PCT Pub. No.: WO2014/148377
PCT Pub. Date: Sep. 25, 2014

(65) Prior Publication Data
US 2016/0272952 A1    Sep. 22, 2016

(30) Foreign Application Priority Data
Mar. 19, 2013    (JP) .................................. 2013-056247

(51) Int. Cl.
| | |
|---|---|
| *C12P 13/12* | (2006.01) |
| *C12N 1/20* | (2006.01) |
| *C12N 9/10* | (2006.01) |
| *C12N 15/70* | (2006.01) |

(52) U.S. Cl.
CPC ........... *C12N 9/1085* (2013.01); *C12N 15/70* (2013.01); *C12P 13/12* (2013.01); *C12Y 205/01047* (2013.01)

(58) Field of Classification Search
CPC ..................... C12N 9/1085; C12Y 205/01047
USPC ............................................. 435/113, 252.3
See application file for complete search history.

(56) References Cited

U.S. PATENT DOCUMENTS

| | | |
|---|---|---|
| 8,278,075 B2 | 10/2012 | Nonaka et al. |
| 8,293,506 B2 | 10/2012 | Nonaka et al. |
| 2005/0124049 A1 | 6/2005 | Ziyatdinov et al. |
| 2010/0216196 A1 | 8/2010 | Nonaka et al. |
| 2010/0233765 A1 | 9/2010 | Nonaka |
| 2011/0033902 A1 | 2/2011 | Nonaka et al. |
| 2012/0252076 A1 | 10/2012 | Yamazaki et al. |

FOREIGN PATENT DOCUMENTS

| | | |
|---|---|---|
| CA | 2386539 A1 | 4/2001 |
| EP | 1220940 A1 | 7/2002 |
| EP | 1571223 A2 | 9/2005 |
| EP | 2246420 A1 | 11/2010 |
| JP | 2005137369 | 6/2005 |
| JP | 2010193788 | 9/2010 |
| JP | 2010207194 | 9/2010 |
| WO | 2009104731 | 8/2009 |
| WO | 2012137689 | 10/2012 |

OTHER PUBLICATIONS

Kredich, "Biosynthesis of Cysteine", Cellular and Mollecular Bilogy, 1996, pp. 514-527.
Sekowska et al., "Sulfur Metabolism in *Escherichia coli* and Related Bacteria: Facts and Fiction", Journal of Molecular Microbiology and Biotechnology, 2000, vol. 2, No. 2, pp. 145-177.
Extended European Search Report for EP Application No. 14771133.7 dated Jul. 18, 2016.
Sirko, Agnieszka, et al., "Sulfate and Thiosulfate Transport in *Escherichia coli* K-12: Nucloetide Sequence and Expression of the cysTWAM Gene Cluster", Journal of Bacteriology, Jun. 1990, vol. 172, No. 6, pp. 3351-3357.
Hryniewicz, Monika, et al., "Sulfate and Thiosulfate Transport in *Escherichia coli* K-12: Identification of a Gene Encoding a Novel Protein Involved in Thiosulfate Binding", Journal of Bacteriology, Jun. 1990, vol. 172, No. 6, pp. 3358-3366.
Nakatani, Takeshi, et al., "Enhancement of Thioredoxin/Glutaredoxin-Mediated L-cysteine Synthesis from S-sulfocysteine Increases L-cysteine Production in *Escherichia coli*", Microbial Cell Factories, 2012, vol. 11, No. 62, pp. 1-9.
International Search Report based on International Application No. PCT/JP2014/056872, dated Jun. 17, 2014.

*Primary Examiner* — Tekchand Saidha
(74) *Attorney, Agent, or Firm* — McCarter & English, LLP (57) ABSTRACT

L-cysteine can be produced inexpensively and efficiently by using a bacterium belonging to the family Enterobacteriaceae modified to reduce activity of O-acetylserine sulfhydrylase B thereof, the bacterium being modified so that the C terminal region of its thiosulfate-binding protein is deleted, and the bacterium having an increased ability to produce L-cysteine in the presence of a sulfate.

18 Claims, 3 Drawing Sheets

■ sup1_pDES(+SO₄)
□ ΔcysM_pDES(+SO₄)

Fig. 5

■ sup1_pDES(+S₂O₃+SO₄)
□ ΔcysM_pDES(+S₂O₃+SO₄)

ENTEROBACTERIACEAE BACTERIA EXHIBITING INCREASED L-CYSTEINE PRODUCING ABILITY

CROSS-REFERENCE TO RELATED APPLICATIONS

This application is a national stage application filed under 35 USC 371 of PCT/JP2014/056872, filed Mar. 14, 2014, which claims the benefit of Japanese Patent Application No. 2013-056247, filed Mar. 19, 2013, all of which are incorporated herein, in entirety, by reference.

TECHNICAL FIELD

The present invention relates to a bacterium belonging to the family Enterobacteriaceae, the bacterium having an increased ability to produce L-cysteine in the presence of a sulfate, and to a method for producing L-cysteine using the bacterium.

BACKGROUND ART

Cysteines and cystines are used in a wide variety of fields, such as pharmaceutical products, cosmetics, and foods. Since cysteine is an amino acid present in high concentrations mainly in human and animal hair, it has been classically produced by hydrolyzing such hair. However, production of cysteine by fermentation is desired, as with many other amino acids, from the viewpoint of higher product safety and less environmental impact.

Various methods for producing cysteine by fermentation using bacteria belonging to the family Enterobacteriaceae have been reported (Patent Literature 1 and 2). For example, *Escherichia coli*, which is a bacterium belonging to the family Enterobacteriaceae, has two cysteine biosynthesis pathways: a pathway using a sulfate as a sulfur source (sulfate pathway) and a pathway using a thiosulfate as a sulfur source (thiosulfate pathway) (Non-patent Literature 1).

When cysteine is produced using bacteria belonging to the family Enterobacteriaceae, it is known that, in general, cysteine cannot be efficiently produced even if a medium containing only a sulfate as a sulfur source is used, but that cysteine can be more efficiently produced when a medium containing not only a sulfate but also a thiosulfate as sulfur sources is used.

However, thiosulfates used as sulfur sources are very expensive compared with sulfates. Therefore, there is a need for the development of methods for efficiently producing cysteine using an inexpensive sulfate as a sulfur source.

CITATION LIST

Patent Literature

PTL 1: WO2009/104731
PTL 2: JP2010-193788A

Non-Patent Literature

NPL 1: Nakatani et al., Enhancement of thioredoxin/glutaredoxin-mediated L-cysteine synthesis from S-sulfocysteine increases L-cysteine production in *Escherichia coli*, Microbial Cell Factories, 2012, 11:62

SUMMARY OF INVENTION

Technical Problem

An object of the present invention is to provide a bacterium belonging to the family Enterobacteriaceae, the bacterium having an increased ability to produce L-cysteine in the presence of a sulfate, and a method for producing L-cysteine using the bacterium inexpensively and efficiently.

Solution to Problem

The present inventors conducted extensive research and found that an *Escherichia coli* mutant strain that is deficient in O-acetylserine sulfhydrylase B and in which the C terminal region of its thiosulfate-binding protein is deleted exhibits a high ability to produce L-cysteine even in a medium containing only a sulfate as a sulfur source. The inventors further found that the ability to produce L-cysteine in the mutant strain is improved by culturing in a medium containing not only a sulfate, but also a thiosulfate as sulfur sources. The inventors conducted further research based on these findings, thereby accomplishing the present invention.

More specifically, the present invention includes the following embodiments.

Item 1. A bacterium belonging to the family Enterobacteriaceae modified to reduce activity of O-acetylserine sulfhydrylase B thereof, the bacterium being modified so that the C terminal region of its thiosulfate-binding protein is deleted, and the bacterium having an increased ability to produce L-cysteine in the presence of a sulfate.

Item 2. The bacterium according to Item 1, wherein the thiosulfate-binding protein is a protein set forth in the following (a) or (b),
(a) a protein consisting of the amino acid sequence set forth in SEQ ID NO: 1 or
(b) a protein consisting of an amino acid sequence having at least 85% identity to the amino acid sequence set forth in SEQ ID NO: 1, the protein having thiosulfate-binding activity.

Item 3. The bacterium according to Item 2, wherein the C terminal region is a region set forth in the following (c) or (d),
(c) a region comprising a region consisting of the 274th to 300th amino acids of the amino acid sequence set forth in SEQ ID NO: 1, or
(d) a region that is present in the amino acid sequence having at least 85% identity to the amino acid sequence set forth in SEQ ID NO: 1 and that corresponds to a region comprising a region consisting of the 274th to 300th amino acids of the amino acid sequence set forth in SEQ ID NO: 1.

Item 4. The bacterium according to any one of items 1 to 3, wherein the O-acetylserine sulfhydrylase B is a protein set forth in the following (e) or (f),
(e) a protein consisting of the amino acid sequence set forth in SEQ ID NO: 3 or
(f) a protein consisting of an amino acid sequence having at least 85% identity to the amino acid sequence set forth in SEQ ID NO: 3, the protein having O-acetylserine sulfhydrylase B activity.

Item 5. The bacterium according to any one of Items 1 to 4, wherein its gene encoding the O-acetylserine sulfhydrylase B is disrupted.

Item 6. The bacterium according to any one of Items 1 to 5, wherein the bacterium belonging to the family Enterobacteriaceae is an *Escherichia* bacterium.

Item 7. A method for producing L-cysteine, the method comprising collecting L-cysteine from a culture obtained by culturing the bacterium according to any one of Items 1 to 6 in a medium.

Item 8. The method according to Item 7, wherein the medium comprises a sulfate as a sulfur source.

Item 9. The method according to Item 8, wherein the medium further comprises a thiosulfate as a sulfur source.

Advantageous Effects of Invention

The present invention makes it possible to provide a bacterium belonging to the family Enterobacteriaceae, the bacterium having an increased ability to produce L-cysteine in the presence of a sulfate. The use of the bacterium enables L-cysteine to be produced highly efficiently even in a medium containing only a sulfate as a sulfur source. Because sulfates are very inexpensive compared with thiosulfates, this production method is excellent in terms of cost. In addition, L-cysteine can be produced more efficiently by culturing in a medium containing not only a sulfate, but also a thiosulfate as sulfur sources. The production method of the present invention, which uses microbial 1.0 fermentation, is excellent also from the viewpoint of the safety of products obtained by the method and the burden on the environment.

DESCRIPTION OF EMBODIMENTS

1. Bacterium

The present invention relates to a bacterium belonging to the family Enterobacteriaceae modified to reduce the activity of O-acetylserine sulfhydrylase B thereof, the bacterium being modified so that the C terminal region of its thiosulfate-binding protein is deleted, and the bacterium having an increased ability to produce L-cysteine in the presence of a sulfate.

The bacterium belonging to the family Enterobacteriaceae is not particularly limited as long as it has an ability to produce L-cysteine. The bacterium belonging to the family Enterobacteriaceae may be a wild-type strain or a modified strain. As used herein, the ability to produce L-cysteine refers to an ability to accumulate L-cysteine in a medium containing a sulfur source when the bacterium is cultured in the medium. Specific examples of bacteria belonging to the family Enterobacteriaceae include those classified into the family Enterobacteriaceae according to the taxonomy used in the NCBI (National Center for Biotechnology Information) database, such as *Escherichia* bacteria, *Enterobacter* bacteria, *Pantoea* bacteria, *Klebsielia* bacteria, *Serratia* bacteria, *Erwinia* bacteria, *Salmonella* bacteria, and *Moranella* bacteria, and modified strains (or mutant strains) of these bacteria (http://www.ncbi.nlm.nih.gov/Taxonomy/Browser/wwwtax.cgi?id=91347). Preferable examples are *Escherichia* bacteria and modified strains (or mutant strains) of the bacteria.

The *Escherichia* bacteria are not particularly limited. More specifically, it is possible to use those described in the work of Neidhardt et al. (Backmann, B. J. 1996. Derivations and Genotypes of some mutant derivatives of *Escherichia coli* K-12, pp. 2460-2488. Table 1. In F. D. Neidhardt (ed.), *Escherichia coli and Salmonella*: Cellular and Molecular Biology, Second Edition, American Society for Microbiology Press, Washington, D.C.). An example among these is *Escherichia coli*. Specific examples of *Escherichia coli* include *Escherichia coli*, W3110 (ATCC 27325), *Escherichia coli* MG1655 (ATCC 47076), and like *Escherichia coli* derived from the prototype wild-type strain, K12 strain.

In modified strains of bacteria belonging to the family Enterobacteriaceae, a modification that enhances the ability to produce L-cysteine has preferably been made. Such a modification can be made according to a known method.

For example, to enhance the ability to produce L-cysteine in the bacteria, methods that have been used in the breeding coryneform bacteria, *Escherichia* bacteria, or the like can be used, such as obtaining an auxotrophic mutant, an analog-resistant strain, or a metabolic regulation mutant, and creating a recombinant strain in which the expression of an L-cysteine biosynthesis enzyme is enhanced (see *Aminosan Hakko* (Amino Acid Fermentation), Gakkai Shuppan Center (Ltd.), 1st Edition, published May 30, 1986, pp. 77-100). Here, properties such as auxotrophy, analog resistance, and metabolic regulation mutation may be imparted alone or in a combination of two or more in the breeding of L-cysteine-producing bacteria. The expression of L-cysteine biosynthesis enzymes may be enhanced alone or in a combination of two or more. Furthermore, properties such as auxotrophy, analog resistance, and metabolic regulation mutation may be imparted in combination with enhancement of one or more biosynthesis enzymes.

An auxotrophic mutant, L-cysteine analog-resistant strain, or metabolic regulation mutant, each with the ability to produce L-cysteine can be obtained by subjecting a parent strain or a wild-type strain to general mutatagenesis, such as irradiation with X-rays or ultraviolet rays or treatment with a mutagen such as N-methyl-N'-nitro-N-nitrosoguanidine (NTG) or ethyl methanesulfonate (EMS), and selecting, from the obtained mutant strains, those that exhibit auxotrophy, analog resistance, or a metabolic regulation mutation and that have an ability to produce the L-amino acid.

Specific examples of strains modified to enhance the ability to produce L-cysteine include, but are not limited to, strains belonging to the genus *Escherichia*, such as *E. coli* JM15 transformed with multiple kinds of cysE alleles encoding serine acetyltransferase (SAT) resistant to feedback inhibition (U.S. Pat. No. 6,218,168), *E. coli* W3110 in which a gene encoding a protein suitable for excretion of cytotoxic substances is overexpressed (U.S. Pat. No. 5,972,663), an *E. coli* strain in which cysteine desulfhydrase activity is reduced (JPH11-155571A), and *E. coli* W3110 in which the activity of the positive transcriptional control factor of the cysteine regulon encoded by the cysE gene is increased (WO01/27307).

O-acetylserine sulfhydrylase B is an enzyme that works in the thiosulfate pathway, which is a cysteine biosynthesis pathway, in bacteria belonging to the family Enterobacteriaceae and that has activity of synthesizing S-sulfocysteine (cysteine precursor) using O-acetylserine and a thiosulfate as substrates. The O-acetylserine sulfhydrylase B is rot particularly limited as long as it has the above characteristics. Specific examples include a protein consisting of the amino acid sequence set forth in SEQ ID NO: 3 (protein encoded by the *Escherichia coli* cysM gene).

The O-acetylserine sulfhydrylase B is, for example, preferably a protein set forth in the following (e) or (f),
(e) a protein consisting of the amino acid sequence set forth in SEQ ID NO: 3 or
(f) a protein consisting of an amino acid sequence having at least 85% identity to the amino acid sequence set forth in SEQ ID NO: 3, the protein having O-acetylserine sulfhydrylase B activity.

In (f) above, the identity is preferably 90% or more, more preferably 95% or more, even more preferably 97% or more, still more preferably 98% or more, and particularly preferably 99% or more.

An example of the protein set forth in (f) above is a protein set forth in (f'),
(f') a protein consisting of the same amino acid sequence as set forth in SEQ ID NO: 3 except that one or a plurality of amino acids is substituted, deleted, added, and/or inserted, the protein having O-acetylserine sulfhydrylase B activity.

In (f'), the plurality of amino acids is, for example, 2 to 30 amino acids, preferably 2 to 15 amino acids, more preferably 2 to 8 amino acids, even more preferably 2 to 5 amino acids, and particularly preferably 2 to 3 amino acids.

In the protein set forth in (f) or (f'), the one or more mutation sites with respect to the amino acid sequence set forth in SEQ ID NO: 3 are not particularly limited as long as the protein has O-acetylserine sulfhydrylase B activity. The mutation sites are preferably sites that do not affect O-acetylserine sulfhydrylase B activity. Such sites can be determined, for example, by comparing the amino acid sequences of O-acetylserine sulfhydrylase B in bacteria belonging to the family Enterobacteriaceae, and using identity or similarity in the bacteria as an index. That is, sites at which identity or similarity is low are presumed to be sites that have low influence (or no influence) on O-acetylserine sulfhydrylase B activity.

The O-acetylserine sulfhydrylase B activity can be measured, for example, according to a known method as follows. The protein of interest expressed in bacteria belonging to the family Enterobacteriaceae is obtained, for example, by purifying it from the bacteria or by purifying it from bacteria into which a gene encoding the protein of interest is introduced, and the O-acetylserine sulfhydrylase B activity is measured by examining whether O-acetylserine is reacted with a thiosulfate in the presence of the obtained protein of interest to form S-sulfocysteine, and examining the degree of formation.

The phrase "reduce activity of O-acetylserine sulfhydrylase B thereof" means that the activity of O-acetylserine sulfhydrylase B is lower than the activity in a non-modified strain, such as a wild-type strain, of the bacterium belonging to the family Enterobacteriaceae. Specific examples of such a state include one in which the number of molecules of O-acetylserine sulfhydrylase B per cell is reduced and one in which the O-acetylserine sulfhydrylase B activity per molecule is reduced. It is desirable that the O-acetylserine sulfhydrylase B activity per cell is reduced to 50% or less, preferably 30% or less, and more preferably 10% or less, compared with a non-modified strain. The term "reduce" encompasses cases where the O-acetylserine sulfhydrylase B activity completely disappears.

The phrase "modified to reduce activity of O-acetylserine sulfhydrylase B thereof" is not particularly limited as long as the bacterium is modified to "reduce activity of O-acetylserine sulfhydrylase B thereof." For example, this phrase means that the bacterium is mutated so that the protein expressed from the gene encoding O-acetylserine sulfhydrylase B on the chromosome does not exhibit O-acetylserine sulfhydrylase B activity (or the activity is reduced) by modifying the gene, or that the bacterium is modified so that the gene encoding O-acetylserine sulfhydrylase B on the chromosome is not expressed (or the expression level of the gene is reduced) by modifying the transcriptional regulatory region of the gene. Such modifications can be performed, for example, by disrupting a gene encoding O-acetylserine sulfhydrylase B or modifying a transcriptional regulatory region, such as a promoter sequence or a Shine-Dalgarno (SD) sequence, according to a known method. More specifically, for example, when a gene encoding O-acetylserine sulfhydrylase B is disrupted, the gene can be disrupted by, for example, deleting a partial sequence of the gene encoding O-acetylserine sulfhydrylase B by using a known genetic engineering technique to prepare a deletion gene encoding O-acetylserine sulfhydrylase B, and transforming a bacterium belonging to the family Enterobacteriaceae with DNA containing the deletion gene to cause homologous recombination between the deletion gene and the gene encoding O-acetylserine sulfhydrylase B on the chromosome. Such gene disruption based on gene substitution using homologous recombination has already been established. Examples include a method using linear DNA, a method using a plasmid containing a temperature sensitive replication origin, and the like (U.S. Pat. No. 6,303,383 or JPH05-007491A). The above gene disruption based on gene substitution using homologous recombination can also be performed using a plasmid having no replication ability in a host.

The gene encoding O-acetylserine sulfhydrylase B is not particularly limited, as long as it is a gene encoding the O-acetylserine sulfhydrylase B described above. Examples include DNA comprising the base sequence set forth in SEQ ID NO: 4 (*Escherichia coli* cysM gene). The gene encoding O-acetylserine sulfhydrylase B may also be DNA that hybridizes under stringent conditions with the base sequence set forth in SEQ ID NO: 4 or with a probe that can be prepared from the base sequence. The phrase "stringent conditions" refers to conditions under which a specific hybrid is formed and a non-specific hybrid is not formed. Examples of such conditions include conditions in which washing is performed once, and more preferably twice or three times, at 60° C. at a salt concentration corresponding to 1×SSC, 0.1% SDS, and preferably 0.1×SSC, 0.1% SDS.

The "bacterium belonging to the family Enterobacteriaceae modified to reduce activity of O-acetylserine sulfhydrylase B thereof" may be a bacterium obtained by modifying the above "bacterium belonging to the family Enterobacteriaceae" so as to "reduce activity of O-acetylserine sulfhydrylase B thereof" as described above, or a bacterium belonging to the family Enterobacteriaceae in which such a modification has already been made. Examples of such bacteria include JW2414 strain in the non-essential gene-deficient strain library of *Escherichia* col. K-12 strain in the National BioResource Project (NBRP: http://www-.shigen.nig.ac.jp/ecoli/strain/top/top.jsp).

The thiosulfate-binding protein is an enzyme that works in the thiosulfate pathway, which is a cysteine synthesis pathway in bacteria belonging to the family Enterobacteriaceae, and that has activity of binding to a thiosulfate outside the cell membrane. The thiosulfate-binding protein is not particularly limited as long as it has the above characteristics. Specific examples include a protein consisting of the amino acid sequence set forth in SEQ ID NO: 1 (protein encoded by the *Escherichia coli* cysP gene), a protein consisting of the amino acid sequence set forth in SEQ ID NO: 5 (protein encoded by the *Salmonella typhimurium* cysP gene), a protein consisting of the amino acid sequence set forth in SEQ ID NO: 6 (protein encoded by the *Kiebsiella pneumoniae* cysP gene), and the like.

The thiosulfate-binding protein is, for example, preferably a protein set forth in the following (a) or (b),
(a) a protein consisting of the amino acid sequence set forth in SEQ ID NO: 1 or
(b) a protein consisting of an amino acid sequence having at least 85% identity to the amino acid sequence set forth in SEQ ID NO: 1, the protein having thiosulfate-binding activity.

In (b) above, the identity is preferably 90% or more, more preferably 95% or more, even more preferably 97% or more, still more preferably 98% or more, and particularly preferably 99% or more. The protein consisting of the amino acid sequence set forth in SEQ ID NO: 5 or 6 has about 95% identity to a protein consisting of the amino acid sequence set forth in SEQ ID NO: 1.

An example of the protein set forth in (b) above is a protein set forth in (b'),
(b') a protein consisting of the same amino acid sequence as set forth in SEQ ID NO: 1 except that one or a plurality of amino acids is substituted, deleted, added, and/or inserted, the protein having thiosulfate-binding activity.

In (b'), the plurality of amino acids is, for example, 2 to 30 amino acids, preferably 2 to 15 amino acids, more preferably 2 to 8 amino acids, even more preferably 2 to 5 amino acids, and particularly preferably 2 to 3 amino acids.

In the protein set forth in (b) or (b'), the one or more mutation sites with respect to the amino acid sequence set forth in SEQ ID NO: 1 are not particularly limited as long as the protein has thiosulfate-binding activity. The mutation sites are preferably sites that do not affect thiosulfate-binding activity. Such sites can be determined, for example, by comparing the amino acid sequences of the thiosulfate-binding protein in bacteria belonging to the family Enterobacteriaceae, and using identity or similarity in the bacteria as an index. That is, sites at which identity or similarity is low are presumed to be sites that have low influence (or no influence) on thiosulfate-binding activity.

The thiosulfate-binding activity can be measured according to a known method.

The C terminal region of the thiosulfate-binding protein is not particularly limited as long as it is a region on the C terminal side of the thiosulfate-binding protein. Specific examples include a region set forth in the following (c) or (d),
(c) a region comprising a region consisting of the 274th to 300th amino acids of the amino acid sequence set forth in SEQ ID NO: 1, or
(d) a region that is present in the amino acid sequence having at least 85% identity to the amino acid sequence set forth in SEQ ID NO: 1 and that corresponds to a region comprising a region consisting of the 274th to 300th amino acids of the amino acid sequence set forth in SEQ ID NO: 1.

In (c) and (d), the "region comprising a region consisting of the 274th to 300th amino acids of the amino acid sequence set forth in SEQ ID NO: 1" is not particularly limited as long as it is a region comprising a region consisting of the 274th to 300th amino acids of the amino acid sequence set forth in SEQ ID NO: 1. Examples include a region comprising a region consisting of the 274th to 300th amino acids of the amino acid sequence set forth in SEQ ID NO: 1, as well as any region within a region consisting of 200th to 338th amino acids, preferably the 220th to 330th amino acids, more preferably the 240th to 320th amino acids, even more preferably the 260th to 310th amino acids, and particularly preferably the 270th to 310th amino acids of the amino acid sequence set forth in SEQ ID NO: 1. The phrase "region . . . that corresponds to" refers to the corresponding region when two sequences are compared using BLAST.

The phrase "modified so that the C terminal region of its thiosulfate-binding protein is deleted" means a state in which the bacterium is modified so that the C terminal region of the thiosulfate-binding protein expressed in the cell is deleted. Specific examples of such a state include one in which the thiosulfate-binding protein whose C terminal region is deleted is expressed from the gene encoding the thiosulfate-binding protein on the chromosome by, for example, modifying the gene. Such a modification can be performed according to, for example, a known gene disruption method using homologous recombination, as in the above modification of a gene encoding O-acetylserine sulfhydrylase B.

The gene encoding the thiosulfate-binding protein is not particularly limited, as long as it is a gene encoding the thiosulfate-binding protein described above. Examples include DNA comprising the base sequence set forth in SEQ ID NO: 2 (*Escherichia coli* cysP gene). The gene encoding the thiosulfate-binding protein may also be DNA that hybridizes under stringent conditions with the base sequence set forth in SEQ ID NO: 2 or with a probe that can be prepared from the base sequence. The phrase "stringent conditions" refers to conditions under which a specific hybrid is formed and a non-specific hybrid is not formed. Examples of such conditions include conditions in which washing is performed once, and more preferably twice or three times, at 60° C. at a salt concentration corresponding to 1×SSC, 0.1% SDS, and preferably 0.1×SSC, 0.1% SDS.

The ability to produce L-cysteine in the presence of a sulfate means ability to produce L-cysteine when culture is performed in a medium containing a sulfate as a sulfur source. The ability to produce L-cysteine in the presence of a sulfate preferably means ability to produce L-cysteine when culture is performed in a medium containing only a sulfate as a sulfur source. The concentration of sulfate is, for example, 0.1 to 100 mM, preferably 1 to 80 mM, more preferably 5 to 80 mM, and even more preferably 10 to 50 mM.

The increased ability to produce L-cysteine in the presence of a sulfate means that the ability to produce L-cysteine in the presence of a sulfate is increased compared with that in a bacterium belonging to the family Enterobacteriaceae that is modified to reduce activity of O-acetylserine sulfhydrylase B thereof and that is not modified so that the C terminal region of its thiosulfate-binding protein is deleted.

Because the ability to produce L-cysteine in the presence of a sulfate is increased in the bacterium of the present invention, L-cysteine can be highly efficiently produced even in a medium containing, for example, only an inexpensive sulfate as a sulfur source.

2. Method for Producing L-Cysteine

The present invention relates to a method for producing L-cysteine, the method comprising collecting L-cysteine from a culture obtained by culturing the bacterium of the present invention in a medium. The present invention also relates to a method for producing L-cysteine, the method comprising culturing the bacterium of the present invention in a medium to obtain a culture liquid, and collecting L-cysteine from the obtained culture liquid.

Examples of the medium include a medium containing a carbon source, a nitrogen source, a sulfur source, inorganic ions, and, if necessary, other organic components. For example, media known as media for culturing bacteria belonging to the family Enterobacteriaceae can be used.

Examples of usable carbon sources include saccharides, such as glucose, fructose, sucrose, molasses, and starch hydrolysate, and organic acids, such as fumaric acid, citric acid, and succinic acid. The carbon sources may be used singly or in a combination of two or more.

Examples of usable nitrogen sources include inorganic ammonium salts, such as ammonium sulfate, ammonium chloride, and ammonium phosphate; organic nitrogen, such as soybean hydrolysate; ammonia gas; aqueous ammonia; and the like. The nitrogen sources may be used singly or in a combination of two or more.

Examples of sulfur sources include inorganic sulfur compounds, such as sulfates, sulfites, sulfide salts, hyposulfites, and thiosulfates. Of these, sulfates are preferable from the viewpoint of their low cost. Preferable examples of sulfates include sodium sulfate and magnesium sulfate. L-cysteine can be produced more efficiently by using a medium containing not only a sulfate, but also a thiosulfate as sulfur sources. The sulfur sources may be used singly or in a combination of two or more.

Bacteria belonging to the family Enterobacteriaceae cannot efficiently use a sulfate as a sulfur source for producing L-cysteine; however, the production method of the present invention makes it possible to efficiently produce L-cysteine although it uses a medium containing a sulfate.

As organic trace nutrients, it is desirable to add a required substance such as vitamin B1, a yeast extract, etc., in appropriate amounts. Other than these, potassium phosphate, magnesium sulfate, iron ions, manganese ions, etc., may be added in small amounts if necessary.

The culture is preferably performed under aerobic conditions for 30 to 90 hours. It is preferable that the culture temperature be controlled to be at 25° C. to 37° C. and that the pH be controlled to be 5 to 8 during the culture. To adjust the pH, inorganic or organic, acidic or alkaline substances, ammonia gas, etc., may be used.

Collection of L-cysteine from the culture can be performed by any combination of a usual ion exchange resin method, a precipitation method, and other known methods.

The production method of the present invention makes it possible to produce L-cysteine inexpensively and efficiently. L-cysteine obtained as described above can be used to produce L-cysteine derivatives. The cysteine derivatives include methylcysteine, ethylcysteine, carbocysteine, S-sulfocysteine, acetylcysteine, and the like.

EXAMPLES

Examples are given below to illustrate the present invention in more detail, but the present invention is not limited to these Examples.

Reference Example 1

Figure 1:
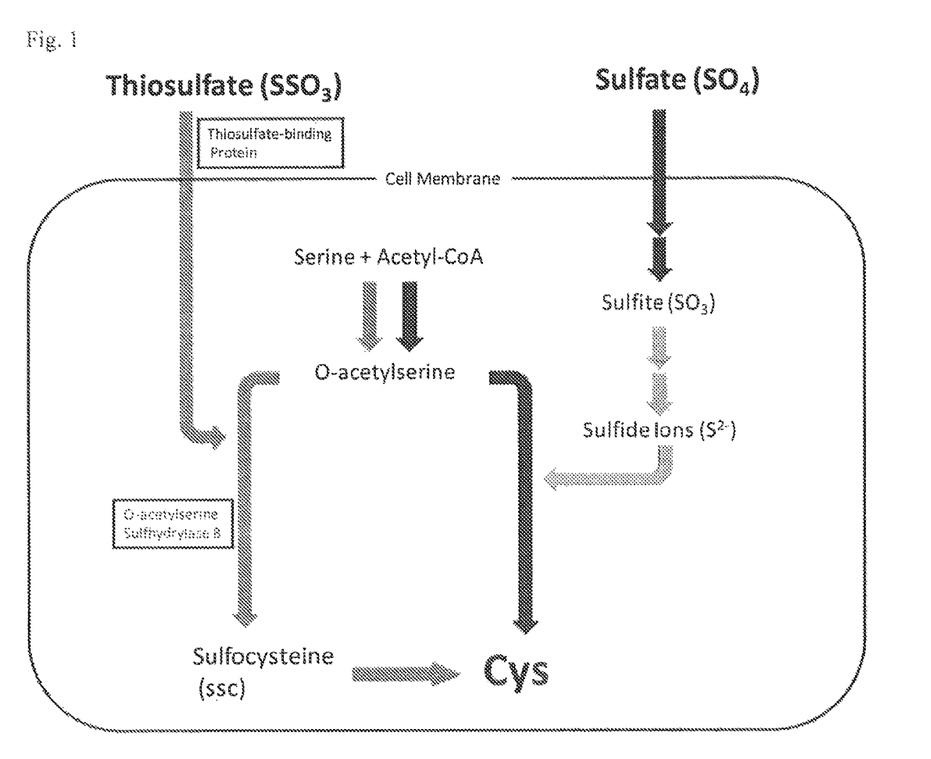
FIG. 1 schematically illustrates the cysteine biosynthesis pathways.

Analysis of Selective Use Mechanism for a Sulfur Source that *Escherichia coli* Uses There are two pathways for *Escherichia coli* to biosynthesize L-cysteine: a pathway that uses a sulfate as a sulfur source (sulfate pathway) and a pathway that uses a thiosulfate as a sulfur source (thiosulfate pathway) (FIG. 1). To clarify part of the selective use mechanism for the two pathways, investigation was made of the sulfur source selectivity of a strain that is deficient in a gene (cysM) encoding an enzyme involved in synthesis of S-sulfocysteine, a precursor of cysteine, (O-acetylserine sulfhydrylase B: FIG. 1) in the thiosulfate pathway. More specifically, the growth performance of the cysM-deficient strain in a medium containing only a sulfate as a sulfur source or in a medium containing both a sulfate and a thiosulfate as sulfur sources was investigated as described below.

A wild-type strain of *Escherichia coli* (BW25113 strain) or a cysM-deficient strain of *Escherichia coli* (JW2414 strain (National BioResource Project, National Institute of Genetics: http://www.shigen.nriig.ac.jp/ecoli/strain/top/top.jsp)) was inoculated into 5 mL of an M9 minimal medium (6 g/L $Na_2HPO_4$, 3 g/L $KH_2PO_4$, 0.5 g/L NaCl, 6 g/L Glucose, 1 mM $MgCl_2$, 0.04% Thiamine-HCl, pH of 7.0), and cultured overnight at 37° C. Each of the resulting culture liquids was diluted 10 fold at each dilution with physiological saline or water to prepare dilution series ($10^{-2}$ to $10^{-8}$). 5 µL of each diluted bacterial liquid was spotted onto an M9 minimal agar medium (1.5% agar) containing only $MgSO_4$ (final concentration of 0.12 g/L) as a sulfur source, an M9 minimal agar medium containing $MgSO_4$ (final concentration of 0.12 g/lL) and $Na_2S_2O_3$ (final concentration of 0.16 g/L) as sulfur sources, or an M9 minimal agar medium containing cystine (final concentration of 0.24 g/L) in addition to these two sulfur sources, and cultured overnight at 37° C. FIG. 1 shows the results.

Figure 2:
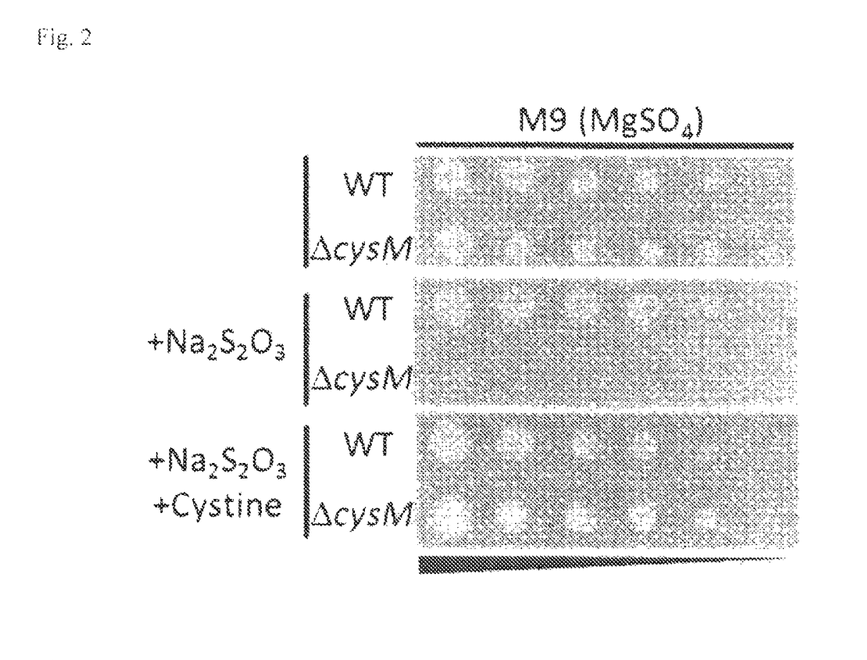
FIG. 2 illustrates inhibition of cysteine biosynthesis through the sulfate pathway by a thiosulfate (thiosulfate repression).

FIG. 2 shows that the cysM-deficient strain (ΔcysM) exhibited growth performance similar to that of the wild-type strain (WT) in the medium containing only a sulfate as a sulfur source (top of FIG. 2). However, the cysM-deficient strain exhibited notably low growth performance compared with that of the wild-type strain in the medium containing a sulfate and a thiosulfate as sulfur sources (middle of FIG. 2). Because the reduction in growth performance was restored by adding cystine in addition to the sulfate and the thiosulfate (bottom of FIG. 2), it was found that the reduction in growth performance was due to a deficiency of cysteine.

O-acetylserine sulfhydrylase B encoded by cysM is an enzyme that synthesizes S-sulfocysteine (cysteine precursor) from a thiosulfate that has entered cells and O-acetylserine. Thus, it is believed that when the cysM-deficient strain, in which this enzyme is not present, is cultured in the presence of a thiosulfate, synthesis of cysteine does not take place through the thiosulfate pathway, thus accumulating the thiosulfate in the cells. On the other hand, since no mutations occur in the sulfate pathway of the cysM-deficient strain, synthesis of cysteine through the sulfate pathway should normally take place. However, as shown in FIG. 2, although the cysM-deficient strain grew normally in the medium containing only a sulfate as a sulfur source, the growth performance was notably reduced in the medium containing not only a sulfate, but also a thiosulfate by a deficiency of cysteine. This means that the thiosulfate accumulated in the cells of the cysM-deficient strain inhibits synthesis of cysteine through the sulfate pathway.

Thus, even if the wild-type strain is cultured in a medium containing both a sulfate and a thiosulfate as sulfur sources, synthesis of cysteine through the sulfate pathway is inhibited by the thiosulfate that enters the cells (this mechanism may be referred to as "thiosulfate repression (TSR)"), which strongly suggests that synthesis of cysteine takes place mainly through the thiosulfate pathway.

Example 1

Preparation of Mutant Strain in which Thiosulfate Repression does not Occur

It is suggested that even if both a sulfate and a thiosulfate are present as sulfur sources, only the thiosulfate is actually used in synthesis of cysteine (Reference Example 1). It is believed that if a mutant strain in which synthesis of cysteine takes place through both the sulfate pathway and the thiosulfate pathway even in a state that both a sulfate and a thiosulfate are present (mutant strain in which thiosulfate repression does not occur) is obtained, cysteine can be synthesized efficiently by using this mutant strain. Thus, preparation of such a mutant strain was attempted. More specifically, it was attempted as described below.

Figure 3:
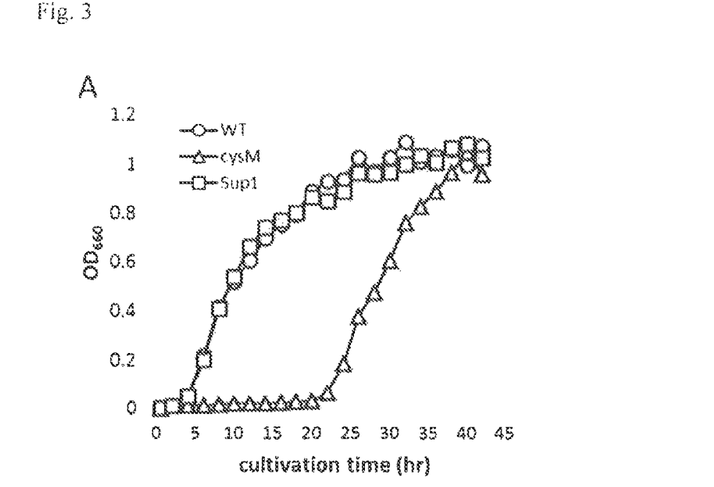
FIG. 3 illustrates a growth curve of a mutant strain in which thiosulfate repression does not occur (suppressor mutant strain).

A cysM-deficient strain of *Escherichia coli* was inoculated into 5 mL of a M9 minimal medium containing $MgSO_4$ (final concentration of 0.12 g/L) and $Na_2S_2O_3$ (final concentration of 0.16 g/L) as sulfur sources ("M9 minimal medium ($SO_4+$, $S_2O_3+$)"), and cultured at 37° C. for 40 hours. FIG. 3 shows the growth curve of the cysM-deficient strain in the culture (cysM in FIG. 3). FIG. 3 reveals that almost no growth of the cysM-deficient strain was observed until about 22 hours after the start of the culture when the strain was cultured in the presence of the sulfate and the thiosulfate; after that, however, the strain gradually grew and eventually grew to a turbidity similar to that of the wild-type strain. From this result, it is believed that a mutant strain in which thiosulfate repression does not occur was produced from the cysM-deficient strain in the culture. Thus, the culture liquid was plated on an agar medium of M9 minimal medium ($SO_4+$, $S_2O_3+$) and cultured overnight, and then, single colonies of the mutant strain were separated from the agar medium. The separated mutant strain was inoculated into 5 mL of an M9 minimal medium ($SO_4+$, $S_2O_3+$), and cultured at 37'C for 40 hours. FIG. 3 shows the growth curve of the mutant strain in the culture (Sup 1 in FIG. 3). FIG. 3 reveals that the turbidity increased in the culture liquid of the mutant strain about 4 hours after the start of the culture. This was growth performance similar to that of the wild-type strain (WT in FIG. 3). As described above, because the obtained mutant strain exhibited growth performance similar to that of the wild-type strain even when it was cultured in the presence of the sulfate and the thiosulfate, it is a mutant strain in which thiosulfate repression does not occur (this mutant strain may be referred to as "suppressor mutant strain (Sup 1)."

Example 2

Analysis of Mutation Sites of the Suppressor Mutant Strain

To identify the site of the suppressor mutant strain obtained in Example 1 that is mutated from the cysM-deficient strain, the genomes of these strains were analyzed using a next-generation sequencer. More specifically, the analysis was performed as described below.

The genome of the suppressor mutant strain and the genome of the cysM-deficient strain were extracted and purified, and the obtained genomes were resequenced using a 454 GS junior (produced by Roche). As a result, in both strains, nearly 200,000 long reads having an average length of about 480 bp were obtained. About 84 Mbp of sequence information was obtained in the cysM-deficient strain, and about 98 Mbp of sequence information was obtained in the suppressor mutant strain (Table 9). In view of the fact that the genome size of *Escherichia coli* is about 5 Mbp, such amounts of genomic information were considered to be sufficient to analysis of mutation sites, i.e., about 16 times the amount of the *Escherichia coli* genome in the cysM-deficient strain and about 20 times the amount of the *Escherichia coli* genome in the suppressor mutant strain. An average length of reads was 480 bp, which is longer than when other next-generation sequencers such as Solid are used.

The genome of the wild-type strain (BW25113 strain), which is a parent strain of the cysM-deficient strain, has not been determined. Therefore, the genomic information obtained with the 454 GS junior was mapped to genomic information of MG1655 strain, which is considered to be a closely related strain of BW25113 strain, and SNPs and mutations of 20 bp or more were compared between the genome of the suppressor mutant strain and the genome of the cysM-deficient strain.

The results of analysis of SNPs reveal that there was no difference in SNPs between the cysM-deficient strain and the suppressor mutant strain with respect to MG1655. As a result of comparing mutations of 20 bp or more, it was found that, interestingly, there was 81 bp deletion in the cysP gene, which is a Cys synthesis-related gene, only in the suppressor mutant strain. More specifically, the 820th to 900th nucleotides (81 bp) in SEQ ID NO: 2, which represents the ORF of the cysP gene, were deleted. This deleted region corresponds to a region of the 274th to 300th amino acids in SEQ ID NO: 1, which represents the amino acid sequence of thiosulfate-binding protein encoded by the cysP gene.

Example 3

Ability to Produce Cysteine the Suppressor Mutant Strain

The ability to produce cysteine in the suppressor mutant strain was investigated. More specifically, it was investigated as described below.

A plasmid that improves an ability to produce cysteine (pDES) was introduced into the cysM-deficient strain and the suppressor mutant strain. pDES has a structure in which the serA gene mutated so that the 410th amino acid (threonine) is converted to a stop codon, the ydeD gene, and the cysE gene mutated so that the 167th amino acid (threonine) is converted to alanine are inserted under the control of OmpA promoter in pACYC184 plasmid. Feedback inhibition is reduced due to the mutant serA gene and the mutant cysE gene, and excretion of cysteine out of cells is promoted by the ydeD gene. Each of the resulting strains (cysM-deficient strain (pDES+) and suppressor mutant strain (pDES+)) was inoculated into 20 mL of an LB(+Tet) medium (1% Bacto trypton, 0.5% yeast extract, 1% NaCl, 10 μg/ml tetracycline) and pre-cultured at 30° C. for 18 to 22 hours to a stationary phase. The $OD_{660}$ of each stationary phase culture liquid was measured, and each strain was inoculated at $OD_{660}$ of 0.4-1% seed into 30 mL of an SM1 (+10% LB+Tet) medium (0.1 M $KH_2PO_4$—$K_2HPO_4$ buffer (pH of 7.0), 30 g/L glucose, 10 g/L $(NH_4)_2SO_4$, 0.1 g/L NaCl, 7.2 μM $FeSO_4.7H_2O$, 0.6 μM $Na_2MoO_4$, 40.4 μM $H_3BO_3$, 2.9 μM $CoCl_2$, 1 μM $CuSO_4$, 8.1 μM $MnCl_2$, 1 mM $MgSO_4$, 0.1 mM $CaCl_2$, 10% LB medium, 12.5 μg/ml tetracycline). After the inoculation, 0.6 g of $CaCO_3$ was added to prevent a reduction in pH caused by acetic acid synthesized at the same time with Cys. As a sulfur source, $MgSO_4$ alone or both $Na_2S_2O_3$ and $MgSO_4$ were used.

Figure 4:
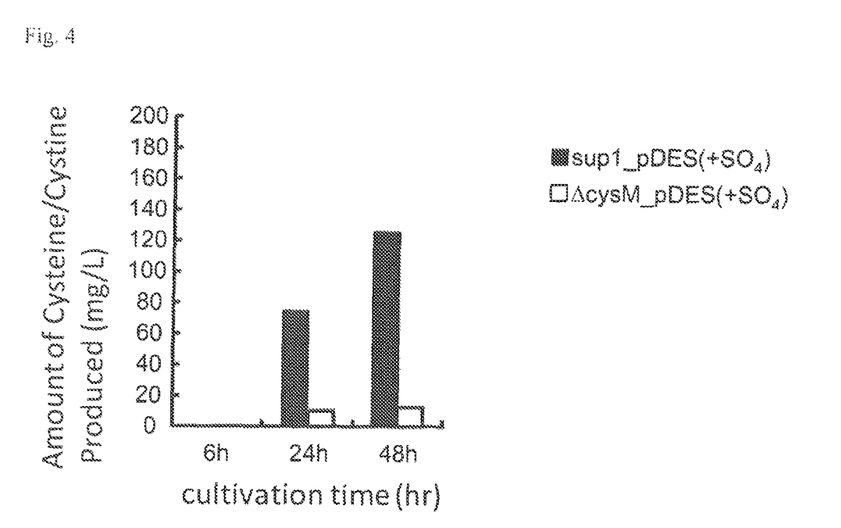
FIG. 4 illustrates the ability to produce cysteine in the suppressor mutant strain in a medium containing only a sulfate as a sulfur source.
Figure 5:
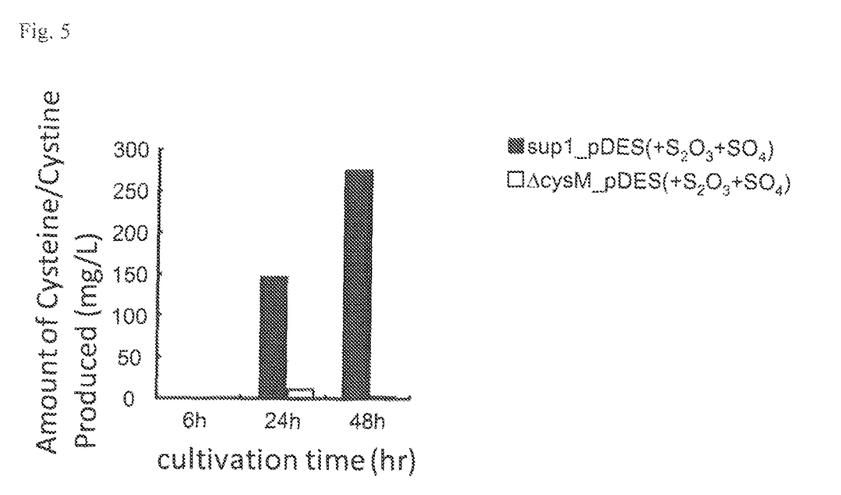
FIG. 5 illustrates the ability to produce cysteine in the suppressor mutant strain in a medium containing not only a sulfate, but also a thiosulfate as sulfur sources.

Na$_2$S$_2$O$_3$ was added to a final concentration of 20 mM after 6 hours cultivation. 600 μL of each was sampled every 12 hours after the start of the culture. 40 μL of each sample was suspended in 1 mL of 0.1N hydrochloric acid (to dissolve CaCO$_3$ contained in the medium), and the OD$_{562}$ of each sample was measured to examine growth. The remainder of each sample was centrifuged at 12,000 rpm to collect a culture medium supernatant, and then the Cys accumulation amount was measured. The measurement of the Cys accumulation amount was performed by the acidic ninhydrin method (Gaitonde et al., 1967). 50 μL of each culture medium supernatant was reacted with 50 μL of 10 mM DTT (pH of 8.6) for 10 minutes, and 100 μL of acetic acid and 100 μL of 12 N hydrochloric acid were added. Each mixture was stirred and heated at 105° C. for 20 minutes. After the heating, each of the resulting mixtures was cooled, and 1.5 mL of ethanol was added. The OD$_{560}$ of each mixture was measured, and the Cys accumulation amount was examined from a Cys calibration curve prepared in advance. FIG. 4 shows the results obtained when MgSO$_4$ alone was added as a sulfur source. FIG. 5 shows the results obtained when both Na$_2$S$_2$O$_3$, and MgSO$_4$, were added.

FIG. 4 reveals that the suppressor mutant strain (sup 1_pDES(+SO$_4$) in FIG. 4) exhibited a much higher ability to produce cysteine than the cysM-deficient strain (ΔcysM_pDES(+SO$_4$) in FIG. 4), which is the parent strain, in the medium containing only the sulfate as a sulfur source. It was completely unexpected that the suppressor mutant strain, which was selected by using an indicator that thiosulfate repression does not occur, exhibited a higher ability to produce cysteine than the cysM-deficient strain even in the absence of thiosulfate (thiosulfate repression does not occur in the first place). Because the sulfate pathway for synthesis of cysteine in the cysM-deficient strain was intact, the ability to produce cysteine in the cysM-deficient strain in the medium containing only the sulfate as a sulfur source was similar to that of the wild-type strain. Thus, the results shown in FIG. 4 reveal that cysteine production using a sulfate as a sulfur source can be performed more efficiently in the suppressor mutant strain than in the wild-type strain.

FIG. 5 reveals that the suppressor mutant strain (sup 1_pDES(+S$_2$O$_3$+SO$_4$) in FIG. 5) exhibited a much higher ability to produce cysteine than the cysM-deficient strain (ΔcysM_pDES(+S$_2$O$_3$+SO$_4$) in FIG. 5), which is the parent strain, in the medium containing bath the sulfate and the thiosulfate as sulfur sources. The ability to produce cysteine in the suppressor mutant strain when the medium contained both the sulfate and the thiosulfate as sulfur sources was higher than that when the medium contained only the sulfate as a sulfur source (comparison of the results shown in the ordinates of FIG. 4 and FIG. 5). More specifically, the ability to produce cysteine in the suppressor mutant strain was improved by further adding the thiosulfate in addition to the sulfate. The suppressor mutant strain is a strain in which two genes that work in the thiosulfate pathway are mutated (the strain is deficient in one of the two genes). Thus, it was completely unexpected that the ability to produce cysteine was improved by the thiosulfate.

We claim:

1. A bacterium belonging to the family Enterobacteriaceae modified to reduce activity of O-acetylserine sulfhydrylase B thereof, the bacterium being modified so that the C terminal region of its thiosulfate-binding protein is deleted, and the bacterium having an increased ability to produce L-cysteine in the presence of a sulfate.

2. The bacterium according to claim 1, wherein the thiosulfate-binding protein is a protein set forth in the following (a) or (b),
   (a) a protein consisting of the amino acid sequence set forth in SEQ ID NO: 1; or
   (b) a protein consisting of an amino acid sequence having at least 85% identity to the amino acid sequence set forth in SEQ ID NO: 1;
and wherein the protein has thiosulfate-binding activity.

3. The bacterium according to claim 2, wherein the C terminal region is a region set forth in the following (c) or (d),
   (c) a region comprising a region consisting of the 274$^{th}$ to 300$^{th}$ amino acids of the amino acid sequence set forth in SEQ ID NO: 1, or
   (d) a region that is present in the amino acid sequence having at least 85% identity to the amino acid sequence set forth in SEQ ID NO: 1 and that corresponds to a region comprising a region consisting of the 274$^{th}$ to 300$^{th}$ amino acids of the amino acid sequence set forth in SEQ ID NO: 1.

4. The bacterium according to claim 1, wherein the O-acetylserine sulfhydrylase B is a protein set forth in the following (e) or (f),
   (e) a protein consisting of the amino acid sequence set forth in SEQ ID NO: 3; or
   (f) a protein consisting of an amino acid sequence having at least 85% identity to the amino acid sequence set forth in SEQ ID NO: 3; and
wherein the protein has O-acetylserine sulfhydrylase B activity.

5. The bacterium according to claim 1, wherein its gene encoding the O-acetylserine sulfhydrylase B is disrupted.

6. The bacterium according to claim 1, wherein the bacterium belonging to the family Enterobacteriaceae is an *Escherichia* bacterium.

7. A method for producing L-cysteine, the method comprising collecting L-cysteine from a culture obtained by culturing the bacterium according to claim 1 in a medium.

8. The method according to claim 7, wherein the medium comprises a sulfate as a sulfur source.

9. The method according to claim 8, wherein the medium further comprises a thiosulfate as a sulfur source.

10. The bacterium according to claim 2, wherein the O-acetylserine sulfhydrylase B is a protein set forth in the following (e) or (f),
    (e) a protein consisting of the amino acid sequence set forth in SEQ ID NO: 3; or
    (f) a protein consisting of an amino acid sequence having at least 85% identity to the amino acid sequence set forth in SEQ ID NO: 3; and
wherein the protein has O-acetylserine sulfhydrylase B activity.

11. The bacterium according to claim 3, wherein the O-acetylserine sulfhydrylase B is a protein set forth in the following (e) or (f),
    (e) a protein consisting of the amino acid sequence set forth in SEQ ID NO: 3; or
    (f) a protein consisting of an amino acid sequence having at least 85% identity to the amino acid sequence set forth in SEQ ID NO: 3; and
wherein the protein has O-acetylserine sulfhydrylase B activity.

12. The bacterium according to claim 2, wherein its gene encoding the O-acetylserine sulfhydrylase B is disrupted.

13. The bacterium according to claim 3, wherein its gene encoding the O-acetylserine sulfhydrylase B is disrupted.

14. The bacterium according to claim 4, wherein its gene encoding the O-acetylserine sulfhydrylase B is disrupted.

15. The bacterium according to claim 2, wherein the bacterium belonging to the family Enterobacteriaceae is an *Escherichia* bacterium.

16. The bacterium according to claim 3, wherein the bacterium belonging to the family Enterobacteriaceae is an *Escherichia* bacterium.

17. The bacterium according to claim 4, wherein the bacterium belonging to the family Enterobacteriaceae is an *Escherichia* bacterium.

18. The bacterium according to claim 5, wherein the bacterium belonging to the family Enterobacteriaceae is an *Escherichia* bacterium.

* * * * *

SEQUENCE LISTING

```
<160> NUMBER OF SEQ ID NOS: 6

<210> SEQ ID NO 1
<211> LENGTH: 338
<212> TYPE: PRT
<213> ORGANISM: Escherichia coli

<400> SEQUENCE: 1

Met Ala Val Asn Leu Leu Lys Lys Asn Ser Leu Ala Leu Val Ala Ser
1               5                   10                  15

Leu Leu Leu Ala Gly His Val Gln Ala Thr Glu Leu Leu Asn Ser Ser
            20                  25                  30

Tyr Asp Val Ser Arg Glu Leu Phe Ala Ala Leu Asn Pro Pro Phe Glu
        35                  40                  45

Gln Gln Trp Ala Lys Asp Asn Gly Gly Asp Lys Leu Thr Ile Lys Gln
    50                  55                  60

Ser His Ala Gly Ser Ser Lys Gln Ala Leu Ala Ile Leu Gln Gly Leu
65                  70                  75                  80

Lys Ala Asp Val Val Thr Tyr Asn Gln Val Thr Asp Val Gln Ile Leu
                85                  90                  95

His Asp Lys Gly Lys Leu Ile Pro Ala Asp Trp Gln Ser Arg Leu Pro
            100                 105                 110

Asn Asn Ser Ser Pro Phe Tyr Ser Thr Met Gly Phe Leu Val Arg Lys
        115                 120                 125

Gly Asn Pro Lys Asn Ile His Asp Trp Asn Asp Leu Val Arg Ser Asp
    130                 135                 140

Val Lys Leu Ile Phe Pro Asn Pro Lys Thr Ser Gly Asn Ala Arg Tyr
145                 150                 155                 160

Thr Tyr Leu Ala Ala Trp Gly Ala Ala Asp Lys Ala Asp Gly Gly Asp
                165                 170                 175
```

Lys Gly Lys Thr Glu Gln Phe Met Thr Gln Phe Leu Lys Asn Val Glu
            180                 185                 190

Val Phe Asp Thr Gly Gly Arg Gly Ala Thr Thr Thr Phe Ala Glu Arg
        195                 200                 205

Gly Leu Gly Asp Val Leu Ile Ser Phe Glu Ser Glu Val Asn Asn Ile
210                 215                 220

Arg Lys Gln Tyr Glu Ala Gln Gly Phe Glu Val Val Ile Pro Lys Thr
225                 230                 235                 240

Asn Ile Leu Ala Glu Phe Pro Val Ala Trp Val Asp Lys Asn Val Gln
                245                 250                 255

Ala Asn Gly Thr Glu Lys Ala Ala Lys Ala Tyr Leu Asn Trp Leu Tyr
            260                 265                 270

Ser Pro Gln Ala Gln Thr Ile Ile Thr Asp Tyr Tyr Arg Val Asn
        275                 280                 285

Asn Pro Glu Val Met Asp Lys Leu Lys Asp Lys Phe Pro Gln Thr Glu
290                 295                 300

Leu Phe Arg Val Glu Asp Lys Phe Gly Ser Trp Pro Glu Val Met Lys
305                 310                 315                 320

Thr His Phe Thr Ser Gly Gly Glu Leu Asp Lys Leu Leu Ala Ala Gly
                325                 330                 335

Arg Asn

<210> SEQ ID NO 2
<211> LENGTH: 1017
<212> TYPE: DNA
<213> ORGANISM: Escherichia coli

<400> SEQUENCE: 2
atggccgtta acttactgaa aagaactca ctcgcgctgg tcgcttctct gctgctggcg      60
ggccatgtac aggcaacgga actgctgaac agttcttatg acgtctcccg cgagctgttt     120 ccgccctga atccgccgtt tgagcaacaa tgggcaaaag ataacggcgg cgacaaactg     180
acgataaaac aatctcatgc cgggtcatca aaacaggcgc tggcgatttt acagggctta     240
aaagccgacg ttgtcactta taaccaggtg accgacgtac aaatcctgca cgataaaggc     300
aagctgatcc cggccgactg gcagtcgcgc ctgccgaata tagctcgcc gttctactcc      360 accatgggct tcctggtgcg taagggtaac ccgaagaata tccacgattg aacgacctg     420 gtgcgctccg acgtgaagct gattttcccg aacccgaaaa cgtcgggtaa cgcgcgttat    480
acctatctgg cggcatgggg cgcagcggat aaagctgacg tggtgacaa aggcaaaacc     540 gaacagttta tgacccagtt cctgaaaaac gttgaagtgt tcgatactgg cggtcgtggc    600
gcgaccacca cttttgccga gcgcggcctg ggcgatgtgc tgattagctt cgaatcggaa    660
gtgaacaaca tccgtaaaca gtatgaagcg cagggctttg aagtggtgat tccgaaaacc    720
aacattctgg cggaattccc ggtggcgtgg gttgataaaa acgtgcaggc caacggtacg    780
gaaaaagccg ccaaagccta tctgaactgg ctctatagcc cgcaggcgca aaccatcatc    840
accgactatt actaccgcgt gaataacccg gaggtgatgg acaaactgaa agacaaattc    900
ccgcagaccg agctgttccg cgtggaagac aaatttggct cctggccgga agtgatgaaa    960
acccacttca ccagcggcgg cgagttagac aagctgttag cggcggggcg taactga     1017

<210> SEQ ID NO 3
<211> LENGTH: 303
<212> TYPE: PRT

<213> ORGANISM: Escherichia coli

<400> SEQUENCE: 3

```
Met Ser Thr Leu Glu Gln Thr Ile Gly Asn Thr Pro Leu Val Lys Leu
1               5                   10                  15
Gln Arg Met Gly Pro Asp Asn Gly Ser Glu Val Trp Leu Lys Leu Glu
            20                  25                  30
Gly Asn Asn Pro Ala Gly Ser Val Lys Asp Arg Ala Ala Leu Ser Met
        35                  40                  45
Ile Val Glu Ala Glu Lys Arg Gly Glu Ile Lys Pro Gly Asp Val Leu
    50                  55                  60
Ile Glu Ala Thr Ser Gly Asn Thr Gly Ile Ala Leu Ala Met Ile Ala
65                  70                  75                  80
Ala Leu Lys Gly Tyr Arg Met Lys Leu Leu Met Pro Asp Asn Met Ser
                85                  90                  95
Gln Glu Arg Arg Ala Ala Met Arg Ala Tyr Gly Ala Glu Leu Ile Leu
            100                 105                 110
Val Thr Lys Glu Gln Gly Met Glu Gly Ala Arg Asp Leu Ala Leu Glu
        115                 120                 125
Met Ala Asn Arg Gly Glu Gly Lys Leu Leu Asp Gln Phe Asn Asn Pro
    130                 135                 140
Asp Asn Pro Tyr Ala His Tyr Thr Thr Thr Gly Pro Glu Ile Trp Gln
145                 150                 155                 160
Gln Thr Gly Gly Arg Ile Thr His Phe Val Ser Ser Met Gly Thr Thr
                165                 170                 175
Gly Thr Ile Thr Gly Val Ser Arg Phe Met Arg Glu Gln Ser Lys Pro
            180                 185                 190
Val Thr Ile Val Gly Leu Gln Pro Glu Glu Gly Ser Ser Ile Pro Gly
        195                 200                 205
Ile Arg Arg Trp Pro Thr Glu Tyr Leu Pro Gly Ile Phe Asn Ala Ser
    210                 215                 220
Leu Val Asp Glu Val Leu Asp Ile His Gln Arg Asp Ala Glu Asn Thr
225                 230                 235                 240
Met Arg Glu Leu Ala Val Arg Glu Gly Ile Phe Cys Gly Val Ser Ser
                245                 250                 255
Gly Gly Ala Val Ala Gly Ala Leu Arg Val Ala Lys Ala Asn Pro Asp
            260                 265                 270
Ala Val Val Val Ala Ile Ile Cys Asp Arg Gly Asp Arg Tyr Leu Ser
        275                 280                 285
Thr Gly Val Phe Gly Glu Glu His Phe Ser Gln Gly Ala Gly Ile
    290                 295                 300
```

<210> SEQ ID NO 4
<211> LENGTH: 912
<212> TYPE: DNA
<213> ORGANISM: Escherichia coli

<400> SEQUENCE: 4

```
gtgagtacat tagaacaaac aataggcaat acgcctctgg tgaagttgca gcgaatgggg      60
ccggataacg gcagtgaagt gtggttaaaa ctgaaggca ataacccggc aggttcggtg     120
aaagatcgtg cggcactttc gatgatcgtc gaggcggaaa agcgcgggga aattaaaccg     180
ggtgatgtct taatcgaagc caccagtggt aacaccggca ttgcgctggc aatgattgcc     240
gcgctgaaag gctatcgcat gaaattgctg atgcccgaca acatgagcca ggaacgccgt     300
```

```
gcggcgatgc gtgcttatgg tgcggaactg attcttgtca ccaaagagca gggcatggaa    360
ggtgcgcgcg atctggcgct ggagatggcg aatcgtggcg aaggaaagct gctcgatcag    420
ttcaataatc ccgataaccc ttatgcgcat tacaccacca ctgggccgga aatctggcag    480
caaaccggcg ggcgcatcac tcattttgtc tccagcatgg ggacgaccgg cactatcacc    540
ggcgtctcac gctttatgcg cgaacaatcc aaaccggtga ccattgtcgg cctgcaaccg    600
gaagagggca gcagcattcc cggcattcgc cgctggccta cggaatatct gccggggatt    660
ttcaacgctt ctctggtgga tgaggtgctg gatattcatc agcgcgatgc ggaaaacacc    720
atgcgcgaac tggcggtgcg ggaaggaata ttctgtggcg tcagctccgg cggcgcggtt    780
gccggagcac tgcgggtggc aaaagctaac cctgacgcgg tggtggtggc gatcatctgc    840
gatcgtggcg atcgctacct ttctaccggg gtgtttgggg aagagcattt tagccagggg    900
gcggggattt aa                                                         912
```

<210> SEQ ID NO 5
<211> LENGTH: 338
<212> TYPE: PRT
<213> ORGANISM: Salmonella typhimurium

<400> SEQUENCE: 5

```
Met Ala Val Asn Leu Leu Lys Lys Arg Pro Leu Thr Leu Ala Ala Met
1               5                   10                  15

Leu Leu Leu Ala Gly Gln Ala Gln Ala Thr Glu Leu Leu Asn Ser Ser
            20                  25                  30

Tyr Asp Val Ser Arg Glu Leu Phe Ala Ala Leu Asn Pro Pro Phe Glu
        35                  40                  45

Gln Gln Trp Ala Lys Asp Asn Gly Gly Asp Lys Leu Thr Ile Lys Gln
    50                  55                  60

Ser His Ala Gly Ser Ser Lys Gln Ala Leu Ala Ile Leu Gln Gly Leu
65                  70                  75                  80

Lys Ala Asp Val Val Thr Tyr Asn Gln Val Thr Asp Val Gln Ile Leu
                85                  90                  95

His Asp Lys Gly Lys Leu Ile Pro Ala Asp Trp Gln Ser Arg Leu Pro
            100                 105                 110

Asn Asn Ser Ser Pro Phe Tyr Ser Thr Met Gly Phe Leu Val Arg Lys
        115                 120                 125

Gly Asn Pro Lys Asn Ile His Asp Trp Ser Asp Leu Val Arg Ser Asp
    130                 135                 140

Val Lys Leu Ile Phe Pro Asn Pro Lys Thr Ser Gly Asn Ala Arg Tyr
145                 150                 155                 160

Thr Tyr Leu Ala Ala Trp Gly Ala Ala Asp Asn Ala Asp Gly Gly Asp
                165                 170                 175

Lys Ala Lys Thr Glu Gln Phe Met Thr Gln Phe Leu Lys Asn Val Glu
            180                 185                 190

Val Phe Asp Thr Gly Gly Arg Gly Ala Thr Thr Thr Phe Ala Glu Arg
        195                 200                 205

Gly Leu Gly Asp Val Leu Ile Ser Phe Glu Ser Glu Val Asn Asn Ile
    210                 215                 220

Arg Lys Gln Tyr Glu Ala Gln Gly Phe Glu Val Val Ile Pro Lys Thr
225                 230                 235                 240

Asn Ile Leu Ala Glu Phe Pro Val Ala Trp Val Asp Lys Asn Val Gln
                245                 250                 255

Ala Asn Gly Thr Glu Lys Ala Ala Lys Ala Tyr Leu Asn Trp Leu Tyr
```

```
                260                 265                 270
Ser Pro Gln Ala Gln Thr Ile Ile Thr His Tyr Tyr Tyr Arg Val Asn
            275                 280                 285

Asn Pro Glu Ile Met Gly Lys Gln Ala Asp Lys Phe Pro Gln Thr Glu
            290                 295                 300

Leu Phe Arg Val Glu Glu Lys Phe Gly Ser Trp Pro Glu Val Met Lys
305                 310                 315                 320

Thr His Phe Ala Ser Gly Gly Glu Leu Asp Lys Leu Leu Ala Ala Gly
                325                 330                 335

Arg Lys

<210> SEQ ID NO 6
<211> LENGTH: 338
<212> TYPE: PRT
<213> ORGANISM: Klebsiella pneumoniae

<400> SEQUENCE: 6

Met Ala Val Lys Ser Leu Lys Lys Gly Tyr Leu Ala Leu Ala Ala Ser
1               5                   10                  15

Met Leu Leu Val Ala Gln Ala Gln Ala Thr Glu Leu Leu Asn Ser Ser
            20                  25                  30

Tyr Asp Val Ser Arg Glu Leu Phe Ala Ala Leu Asn Pro Pro Phe Glu
        35                  40                  45

Gln Gln Trp Ala Lys Asp Asn Gly Gly Asp Lys Leu Thr Ile Lys Gln
    50                  55                  60

Ser His Ala Gly Ser Ser Lys Gln Ala Leu Ala Ile Leu Gln Gly Leu
65                  70                  75                  80

Lys Ala Asp Val Val Thr Tyr Asn Gln Val Thr Asp Val Gln Ile Leu
                85                  90                  95

His Asp Lys Gly Asn Leu Ile Pro Ala Asp Trp Gln Ser Arg Leu Pro
            100                 105                 110

Asn Asn Ser Ser Pro Phe Tyr Ser Thr Met Gly Phe Leu Val Arg Lys
        115                 120                 125

Gly Asn Pro Lys Asn Ile His Asp Trp Asn Asp Leu Val Arg Ser Asp
    130                 135                 140

Val Lys Leu Ile Phe Pro Asn Pro Lys Thr Ser Gly Asn Ala Arg Tyr
145                 150                 155                 160

Thr Tyr Leu Ala Ala Trp Gly Ala Ala Asp Lys Ala Asp Gly Gly Asp
                165                 170                 175

Lys Ala Lys Thr Glu Gln Phe Met Thr Gln Phe Leu Lys Asn Val Glu
            180                 185                 190

Val Phe Asp Thr Gly Gly Arg Gly Ala Thr Thr Thr Phe Ala Glu Arg
        195                 200                 205

Gly Leu Gly Asp Val Leu Ile Ser Phe Glu Ser Glu Val Asn Asn Ile
    210                 215                 220

Arg Lys Gln Tyr Glu Val Gln Gly Phe Glu Val Val Ile Pro Lys Thr
225                 230                 235                 240

Asn Ile Leu Ala Glu Phe Pro Val Ala Trp Val Asp Lys Asn Val Lys
                245                 250                 255

Ala Asn Gly Thr Glu Lys Ala Ala Lys Ala Tyr Leu Asn Trp Leu Tyr
            260                 265                 270

Thr Pro Gln Ala Gln Thr Ile Ile Thr Asp Tyr Tyr Tyr Arg Val Asn
        275                 280                 285

Asn Pro Lys Val Met Asp Ala Leu Lys Asp Lys Phe Pro Gln Thr Glu
```

```
            290                 295                 300
Leu Phe Arg Val Glu Asp Lys Phe Gly Ser Trp Pro Glu Val Met Lys
305                     310                 315                 320

Thr His Phe Ala Ser Gly Gly Glu Leu Asp Lys Leu Leu Ala Ala Gly
                    325                 330                 335

Arg Lys
```